United States Patent [19]

Leonard et al.

[11] Patent Number: 5,527,685

[45] Date of Patent: Jun. 18, 1996

[54] ANTIBODIES TO MACROPHAGE STIMULATING PROTEIN, BIOASSAY AND IMMUNOPURIFICATION METHOD

[75] Inventors: Edward J. Leonard, N. Chevy Chase; Alison H. Skeel, Kensington; Teizo Yoshimura, Frederick; Ettore Appela, Chevy Chase, all of Md.

[73] Assignee: The United States of America as represented by the Secretary of the Department of Health and Human Services, Washington, D.C.

[21] Appl. No.: 76,880

[22] Filed: Jun. 15, 1993

Related U.S. Application Data

[62] Division of Ser. No. 586,085, Sep. 21, 1990, Pat. No. 5,219,991.

[51] Int. Cl.$^6$ .................. G01N 33/53; G01N 33/543; C07K 16/00; C07K 1/14
[52] U.S. Cl. .................. 435/7.2; 435/7.1; 530/388.25; 530/389.3; 530/413; 436/518
[58] Field of Search .................. 530/413, 388.25, 530/389.3; 435/7.1, 7.2; 436/518

[56] References Cited

U.S. PATENT DOCUMENTS 4,847,325  7/1989  Shadle et al. .................. 514/12

FOREIGN PATENT DOCUMENTS 276551  8/1988  European Pat. Off. ........ C07K 13/00

OTHER PUBLICATIONS

Leonard, et al; "A Serum Protein that Stimulates Macrophage Movement, Chemotaxis and Spreading", Exp. Cell Res., vol. 102, pp. 434–438 (1976).
Falk et al.; "A 48–Well Micro Chemotaxis Assembly for Rapid and Accurate Measurement of Leukocyte Migration", J. Immunological Methods, vol. 33, pp. 239–247 (1980).
Leonard, et al.; "Effects of Cell Concentration on Chemotactic Responsiveness of Mouse Resident Peritoneal Macrophages", J. Reticuloendothelial Society, vol. 30, No. 4, pp. 271–282 (1981).
Wang, M–H., et al. J. Leukocyte Biology, 54:289–295, Oct. 1993.
Skeel, A. et al., J. Lueukocyte Biology, 40(3): 279, Abs #79, Sep. 1986.
Leonard, E. J., Exp Cell Research, 114(1):117–26, 1978.
Livingston, D. M., Methods In Enzymology, XXXIV: 723–728, 1974.

*Primary Examiner*—Margaret Parr
*Assistant Examiner*—Susan A. Loring
*Attorney, Agent, or Firm*—Needle & Rosenberg

[57] ABSTRACT

A method of purifying macrophage stimulating protein. Antibodies to macrophage stimulating protein and a bioassay for the detection of antibodies which bind macrophage stimulating protein.

8 Claims, 5 Drawing Sheets

MSP, cleaved by CNBr

```
                5         10        15        20
    CB-5:  P L T G Y E V - L G T L F Q N P Q - G E S L
                                                  ?
```

H-CHAIN, lysylendopeptidase digest

```
    *BU-7:  G E G Y E G T A - T T T A G - P E Q E - D A Q -
                    ?                       ?

BU-8:   F N - E A A G V E V N N A E Y -
            S     Y V D           G E

*BU-11: F L D Q G L D D N Y C R N P D G S E -
                              W

*BU-12: D L R E N G - R N P D G S E A P -
                                      ?

BU-14:  G V Q - Q R W S A E T P - - - Q F -
                      ?         ?
```

L-CHAIN, lysylendopeptidase digest

```
    *BU-5:  C E I A G W G E T K

*BU-9:  V V G G H P G N S P W T V - L - N N Q -
                              ?       ?

BU-12:  F L P A G P D D N - C R N P D G Q -
                D Q A L            ?

BU-13:  D L - E N F - - N P D G S E - -
                                    ?

*BU-16: L E R S V T L N Q R V A L I C L P P E E Y V V -
                                              ?       ?
```

L-CHAIN, alkylated

ANTIBODIES TO MACROPHAGE STIMULATING PROTEIN, BIOASSAY AND IMMUNOPURIFICATION METHOD

BACKGROUND OF THE INVENTION

This application is a divisional of application Ser. No. 07/586,085, filed Sep. 21, 1990, now U.S. Pat. No. 5,219,991.

FIELD OF THE INVENTION

The present invention relates to macrophage stimulating protein (MSP). In particular, the present invention relates to the purification of MSP, to highly purified MSP and antibodies specific thereto.

BACKGROUND INFORMATION

Macrophage stimulating protein (MSP), a component of mammalian blood plasma, makes mouse peritoneal macrophages responsive to chemoattractants such as complement C5a [Leonard et al., Exp. Cell Res. 102:434 (1976) and Leonard et al., Exp. Cell Res. 114:117 (1978)]. MSP also stimulates mouse macrophages to increase their movement and pinocytic activity.

The discovery of MSP was based on the observation that peritoneal macrophages in RPMI 1640 medium did not migrate to C5a unless serum was added to the cell suspension. Sera from different mammals, including mice and man, caused activation.

The low concentration of MSP in serum (less than $1/10^5$ of total serum protein) precluded complete purification by conventional techniques. However, highly purified MSP is required for use in human treatments. A method resulting in highly purified MSP is desirable.

SUMMARY OF THE INVENTION

Accordingly, it is an object of the present invention to provide a method for homogeneous purification of MSP.

It is another object of the present invention to provide purified MSP and antibodies specific thereto. The highly purified MSP and/or antibodies thereto may be used for detection of MSP deficiency states, treating pathogen infections and treatment of disease characterized by macrophage-mediated inflammation.

Various other objects and advantages of the present invention will be apparent to one of ordinary skill in the art from the drawings and the following description of the invention.

In one embodiment, the present invention relates to homogeneous macrophage stimulating protein characterized by a band of 70 kilodaltons on non-reducing sodium dodecyl sulfate polyacrylamide gel electrophoresis (SDS-PAGE), bands of 47 kilodaltons and 22 kilodaltons on reducing SDS-PAGE, the amino acid composition according to Table II and a specific activity of $2\times10^5$ units MSP/mg protein.

In another embodiment, the present invention relates to a monoclonal antibody to MSP of the present invention.

In a further embodiment, the present invention relates to a method of purifying macrophage stimulating protein comprising the application of human serum with a specific activity of about 6 units MSP per mg protein to an anti-MSP immunoaffinity column. After MSP is eluted from the column, it is purified to a specific activity of $2\times10^5$ units/mg protein.

In another embodiment, the present invention relates to a pharmaceutical composition for the treatment of pathogen infection comprising the highly purified MSP of the present invention in a pharmaceutically acceptable carrier, in an amount sufficient to stimulate macrophage activity.

BRIEF DESCRIPTION OF THE DRAWINGS

FIG. 1A: chromatography of MSP eluted from immunoaffinity column. FIG. 1B: re-run of MSP peak.

FIG. 3 shows the partial amino acid sequences of MSP fragments.

FIGS. 4A through 4D: 0, $10^{-11}$M, $10^{-10}$M, and $10^{-9}$M, respectively.

DETAILED DESCRIPTION OF THE INVENTION

Figure 1A:
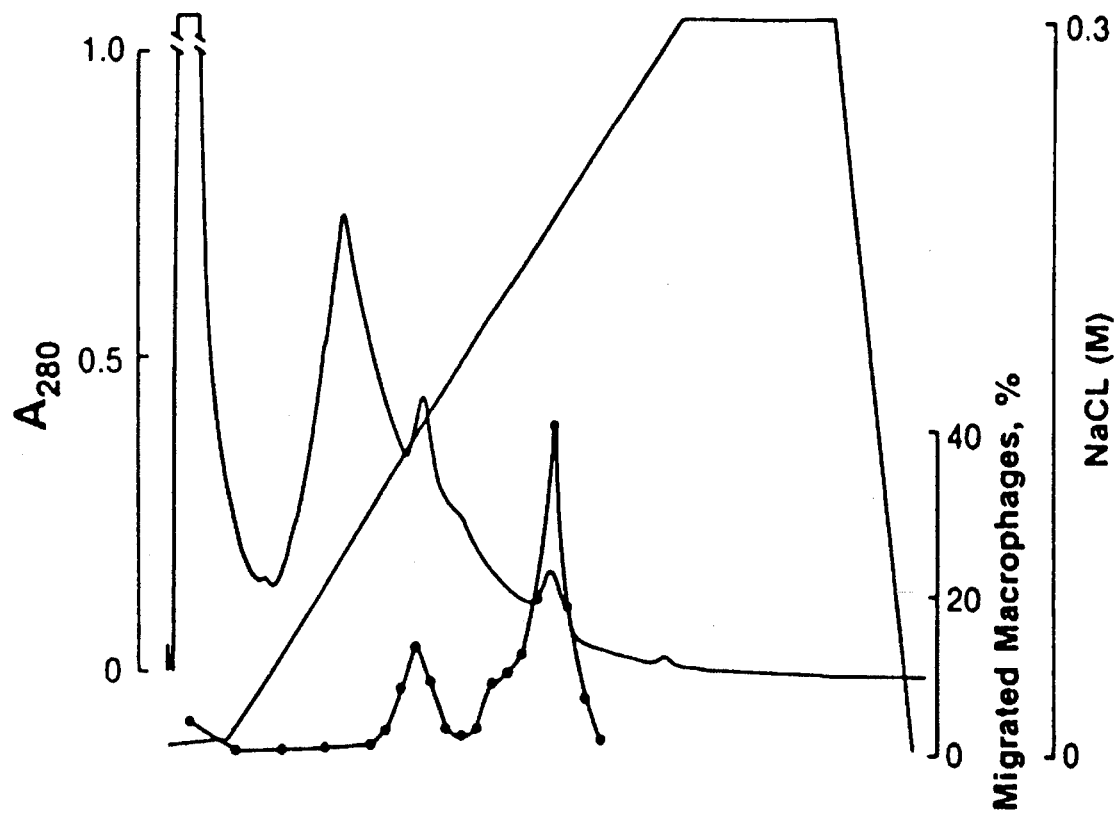
FIGS. 1A–1B shows CM-HPLC purification of MSP.

The present invention relates in part to a method of isolating MSP in a highly pure state. Starting with human serum (having a specific activity of about at least 6 units MSP/mg protein), this invention provides a means of obtaining highly purified MSP. The method involves purification of human serum MSP on an immunoaffinity column of anti-MSP, followed by carboxy methyl high performance liquid chromatography (CM-HPLC), in two sequential runs. The increase in purity resulting from each step of the method of the present invention is shown in Table I as increase in specific activity. The eluted pure MSP is characterized by a specific activity of about $2\times10^5$ units MSP/mg protein. Utilizing this method, MSP has been purified to homogeneity as determined by SDS-PAGE and partial amino acid sequencing of reduced and alkylated α and β chains.

The highly purified MSP is characterized by a band of 70 kilodaltons on non-reducing SDS-PAGE and bands of 47 kilodaltons and 22 kilodaltons on reducing SDS-PAGE. In addition, the MSP has the amino acid composition given in Table II. Further, the highly purified MSP has a specific activity of about $2\times10^5$ units MSP/mg protein.

Peptide fragments of the purified MSP have been sequenced and are shown in FIG. 3. The sequences were compared with the sequences in the Protein Data Bank. The amino acid composition distinguishes the MSP from other known proteins.

The present invention also relates to antibodies (both monoclonal and polyclonal) to MSP. Examples of antibodies belonging to the present invention are the mouse monoclonal IgG anti-MSP antibodies used in the immunoaffinity column (see Examples). Accordingly, the present invention further relates to antibodies to MSP bound to a solid support such as Sepharose gels or polystyrene.

The present invention further relates to bioassays for the detection of MSP or antibodies specific therefor present in a sample such as, for example, a serum sample. Many types of tests, as one skilled in the art will appreciate, can be used for detection. Such tests include, but are not limited to, ELISA.

In an embodiment of the bioassay of the present invention, a surface (ie. a solid support) is coated with the highly purified MSP of the present invention and contacting with the sample (eg. serum). The presence of a resulting complex formed between the coated surface and antibodies specific therefor in the sample can be detected by any of the known methods common in the art, such as an enzyme-conjugated anti-IgG.

The following non-limiting examples are provided to aid in the understanding of the present invention, the true scope of which is set forth in the appended claims. It is understood that modifications can be made in the procedure set forth, without departing from the true spirit of the invention.

EXAMPLES

Throughout the following procedure, MSP was monitored by bioassay [Falk et al., J. Immunol. Methods 37:39 (1980) and Leonard et al., J. Reticuloendothelial Soc. 30:271 (1981)]. Screening for hybridoma antibody was by inhibition of biological activity [Leonard et al., J. Immunol. Methods 82:341 (1985)].

Purification of MSP

Step 1

MSP bioassay

The assay for MSP is based on a concentration-dependent increase in the in vitro chemotactic response of resident peritoneal C3H mouse macrophages to endotoxin-activated mouse serum [Leonard et al., Exp. Cell Res. 102:434 (1976)]. Resident macrophages from peritoneal cavities of normal C3H mice were obtained by lavage with 7–8 ml of RPMI 1640 medium containing 2% BSA. Cells were centrifuged at 4° C. in 50 ml polypropylene tubes for 10 min at 250×g, and resuspended in RPMI 1640 without added protein at a macrophage concentration of $10^6$/ml. For the bioassay, bottom wells of a multiwell chemotaxis chamber [Falk et al., J. Immunol. Methods 37:39 (1980)] were filled with chemoattractant (a 1/200 dilution of endotoxin activated mouse serum) and covered with a 10 μm thick polycarbonate membrane with 5 μm holes. After gasket and top plate were added to complete assembly of the chamber, the upper wells were filled with 50 μl volumes of macrophage suspensions in RPMI 1640 medium containing the stimulating protein to be assayed. During the incubation period of 3 hrs at 37° C. in humidified air with 5% $CO_2$, macrophages migrated through holes in the membrane and remained attached to the attractant side of the membrane. The chamber was then disassembled, and cells were wiped away from the non-migrated side of the membrane. After air drying and staining, migrated cells were counted with an image analyzer [Leonard et al., J. Reticuloendothelial Soc. 30:271 (1981)]. A unit of MSP per ml of test solution was defined as the reciprocal of the dilution required to induce approximately 30% of the maximal chemotactic response obtained at the plateau of the dose-response curve.

Isolation of MSP Antigen for Monoclonal Antibody Production

Large-scale purification of MSP from 3600 ml of outdated frozen plasma (Blood Bank, Clinical Center, NIH, Bethesda) was based in part on published methods [Leonard et al., Exp. Cell Res. 114:117 (1987)]. Plasma was lyophilized and reconstituted to 1/3 of the starting volume. Eight grams of $Na_2SO_4$ per 100 ml of concentrated plasma at 20° C. were added to precipitate unwanted high molecular weight proteins. Supernatant was separated from precipitated protein by centrifugation at 4° C. and divided into 12 aliquots for gel filtration on Sephadex G-200. Fractions with MSP activity eluted from Sephadex G-200 in a region corresponding to a molecular mass of about 100 kD. Pooled fractions from the 12 column runs (1800 ml total) were dialyzed against pH 8.0, 0.005M potassium phosphate buffer and applied to a column containing 170 gm DEAE-cellulose. Unbound protein in the pass-through volume was discarded, and MSP was eluted by a step increase in NaCl concentration to 0.045M in starting buffer. The 380 ml MSP pool was prepared for electrofocusing by lyophilization and reconstitution with water to a volume of 57 ml. This was divided into 3 aliquots for 3 runs on an electrofocusing flat bed. Electrofocused fractions with MSP activity were in the pH range 7.0–7.5. Pooled MSP from each run was dialyzed against 0.0025 M potassium phosphate, pH 7.4, lyophilized, reconstituted with 20 mg/ml sucrose, and run on a 16–550 mm column of Sephadex G-200. Pooled MSP from the 3 Sephadex runs was in a volume of 56 ml, with an $A_{280}$ of 1.5. It was lyophilized, reconstituted with 3 ml of water, and equilibrated with formalin-fixed Cowan strain *S. aureus* (Zymed Laboratories, San Francisco, Calif.) to absorb out traces of IgG.

Step 2

Immunization of Mice, Production of Monoclonal Anti-MSP, and Preparation of Immunoaffinity Column MSP, partially purified as described above and emulsified in complete Freund's adjuvant, was injected intraperitoneally into BALB/c mice. The amount of protein per injection was 280 μg. MSP in incomplete Freund's adjuvant was injected subcutaneously 2 weeks later. The following week, serum from the mice was tested for anti-MSP activity by the capacity of column-bound serum to absorb applied MSP [Leonard et al., J. Immunol. Methods 82:341 (1985)]. Two weeks after this, 0.1 ml of MSP solution was injected intravenously; spleens of the two mice with the most anti-MSP activity were removed four days later. Fusion, cloning and propagation of cell hybrids were done by published methods [Schowalter et al., Inf. Immun. 34:684 (1981)]. Beginning at about 10 days, supernatants from the hybrid cells were tested by an immunoabsorbance assay [Leonard et al., J. Immunol. Methods 82:341 (1985)] for anti-MSP activity. Cells from positive wells were cloned. Several individual clones were obtained that produced IgG anti-MSP. After passage of these clones intraperitoneally in mice, IgG was purified from ascitic fluid on Protein-A Sepharose. The immunoaffinity column for the first purification step was made by the addition of 240 mg of IgG monoclonal anti-MSP to protein-A Sepharose. The column had a diameter of 2.5 cm and a bed height of 8 cm.

Step 3

Purification of MSP Immunoaffinity and HPLC Chromatography

Figure 1B:
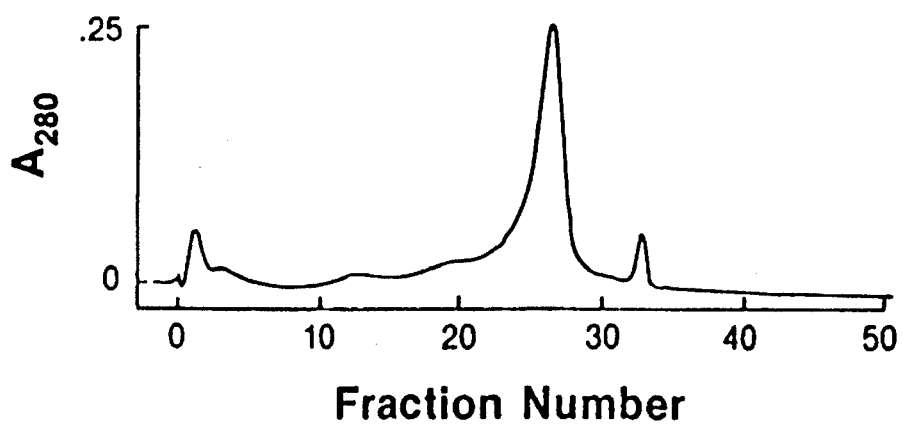

Four 6 liter batches of frozen, outdated human plasma were used for large scale purification of MSP. A 6 liter batch was thawed, filtered through layers of sterile gauze squares, centrifuged at 20° C. for 15 min at 10,000 rpm in a JA-10 rotor in a Beckman J2-21 centrifuge, filtered again through gauze to remove floating lipid, and finally filtered through a glass fiber prefilter (Nalgene 280-5000, Nalge Co., Rochester, N.Y.) supported on a stainless steel mesh on a Millipore suction funnel. The volume of clean plasma was about 5 liters. Plasma was run through the column with a hydrostatic head of about 3 meters, over a period of 4 hrs at 20° C. After the column was rinsed with 0.15M NaCl with 0.05M tris buffer, pH 8.0, MSP was eluted with 0.1M, pH 2.5 glycine buffer. Fractions of 5 ml were collected into tubes containing 1 ml of 0.5M, pH 7.9 potassium phosphate buffer. The $A_{280}$ peak, comprising about 110 ml, was dialyzed at 4° C. overnight against 0.03M NaCl, 0.02M 3-[N-morpholino] propanesulfonic acid, pH 6.7, which was the starting buffer for CM-HPLC. It was centrifuged at 20,000 rpm in a Type 30 rotor of a Beckman L8-70 ultracentrifuge at 5° C., concentrated on an Amicon YM-10 ultrafilter to 2 ml, dialyzed again against starting buffer, and filtered through a 5 ml, 0.45 µm Centrex unit (Schleicher and Schuell, Keene, N.H.). It was then applied to a Beckman Spherogel-TSK CM-3SW dp 10 µm column (7.5 mm×7.5 cm). Running conditions were flow of 1 ml/min, 2 min/fraction, $A_{280}$ absorbance range of 1.28. After the flow-through, a linear gradient of NaCl in starting buffer was run to a limit concentration of 0.3M. Fractions were assayed for MSP biological activity. About 10 fractions were pooled and froze across the MSP peak (HPLC-CM-1 MSP), which was in the region of 0.2M NaCl (FIG. 1, top panel). After 3 more 5 liter batches of plasma were processed as above, the 4 HPLC-CM-1 MSP peaks were pooled, dialyzed against HPLC-CM starting buffer, concentrated to 2 ml, dialyzed against starting buffer again, filtered, and chromatographed on the HPLC-CM column under the same conditions as the first run. Fractions across the $A_{280}$ peak were pooled (HPLC-CM-2 MSP, FIG. 1, bottom panel), to yield pure MSP. Table 1 shown below is a summary of purification and yield of MSP.

TABLE I

Purification and yield of MSP

|  | mg protein | units MSP/ mg protein | total MSP |
|---|---|---|---|
| 5 liters human plasma | $35 \times 10^4$ | 6 | $2 \times 10^6$ |
| Anti-MSP column eluate | 67 | $3 \times 10^3$ | $2 \times 10^5$ |
| HPLC-CM-1 eluate | 1.5 | $7 \times 10^4$ | $1 \times 10^5$ |
| HPLC-CM-2 eluate | 0.6 | $2 \times 10^5$ | $1 \times 10^5$ |

This Table shows that in the first immunoaffinity column step specific activity of MSP increased from 6 to 3000, and total protein decreased from 350 g to about 70 mg. However, MSP was still only about 1 percent of the total protein in this product, as illustrated by drop from 67 to 0.6 mg (with a minimal decrease in total yield) in the HPLC-CM steps.

Characterization of Purified MSP

MSP was characterized by SDS-PAGE under reducing and non-reducing conditions; Western blot analysis, with monoclonal anti-MSP; reduction and alkylation of the α and β chains of MSP, followed by chain separation by gel filtration; amino acid analysis of native MSP, as well as α and β chains; partial amino acid sequence analysis of cyanogen bromide treated MSP, of alkylated MSP β chain, and of purified lysylendopeptidase digest fragments of MSP α and β chains.

Figure 2:
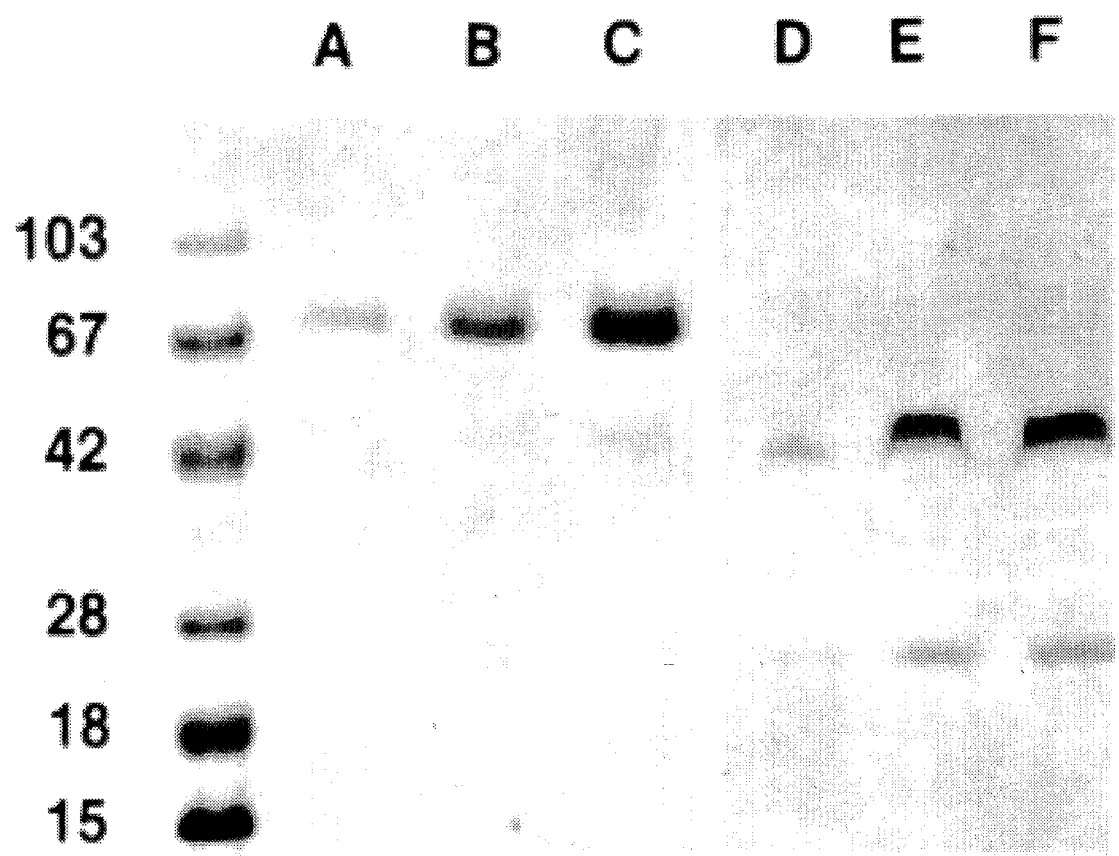
FIG. 2 shows SDS-PAGE of purified HPLC-CM-2 MSP under non reducing (lanes A, B and C) and reducing (lanes D, E and F) conditions. The amounts applied per lane were 125, 250 and 500 ng respectively for lanes A, B and C and D, E, F.
Figure 4A:
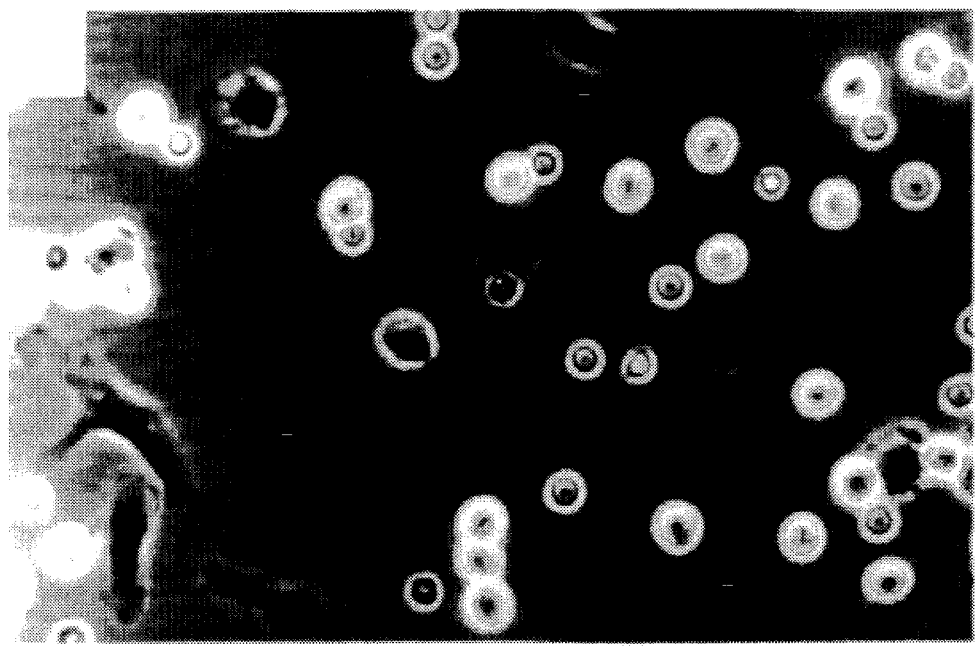
FIGS. 4A–4D shows response of mouse resident macrophages in tissue culture dishes to a 1 hr incubation with pure MSP.
Figure 4B:
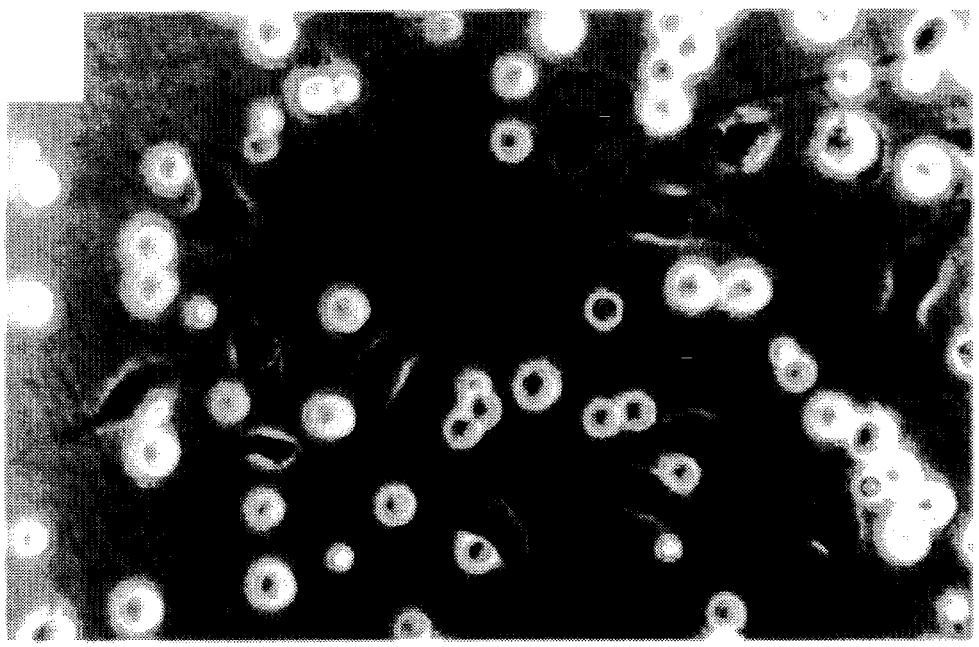
Figure 4C:
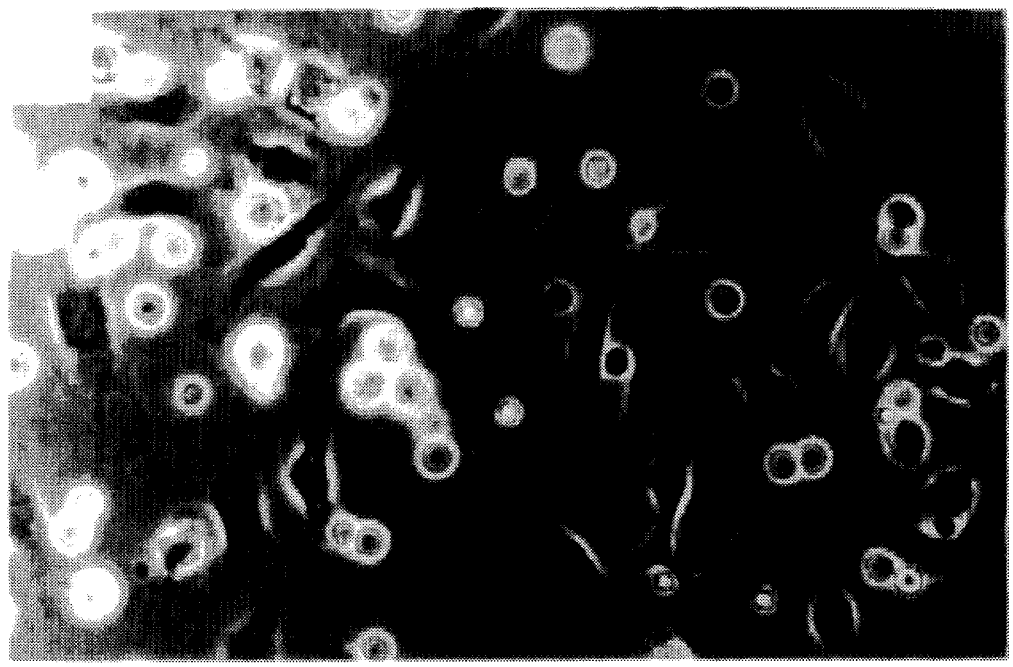
Figure 4D:
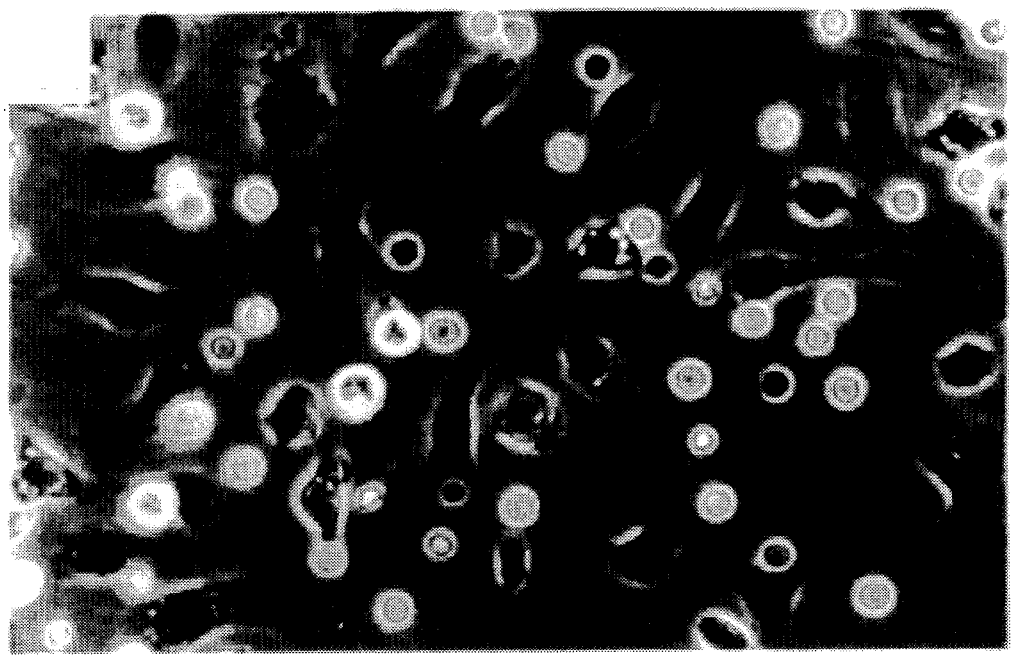

Purified MSP was run on SDS-PAGE under non-reducing (lanes A,B,C,) and reducing (lanes D,E,F) conditions (FIG. 2). The amounts applied per lane were 125, 250, and 500 ng. It was concluded that MSP comprises 2 disulfide-linked chains with molecular masses of approximately 47 and 22 kd. Monoclonal anti-MSP reacted with protein corresponding to the band found on SDS-PAGE under non-reducing conditions. Reactivity was undetectable or minimal with MSP on SDS-PAGE under reducing conditions.

Amino acid composition of MSP and its two chains is shown below in Table II. Partial sequence data are shown in FIG. 3.

The 6 sequences with the fewest ambiguities (indicated by asterisks in FIG. 3) were compared with sequences in the Protein Data Bank. Two of the 6 fragments had highly significant sequence similarities to two known proteins. The first 12 residues of α chain fragment BU-12 matched perfectly with residues 162–173 of bovine prothrombin. BU-12 had only 2/12 mismatches with residues 154–165 and with the approximately repeating residues 259–270 of human prothrombin. The 10-residue β chain fragment BU-5 corresponded, with 3 mismatches, to residues 689–698 of human plasminogen. The partial sequences of MSP comprise about 15 percent of the total molecule. The fragments noted have sequence similarity to two zymogens associated with coagulation systems.

As shown in Table I, pure MSP makes mouse resident peritoneal macrophages responsive to chemoattractant, with an $EC_{30}$ of about $6 \times 10^{-11}$M. FIG. 4 shows the response of mouse resident peritoneal macrophages to a 1 hr incubation with pure MSP. Frames a through d: 0, $10^{-11}$M, $10^{-10}$M and $10^{-9}$M MSP. Greatly elongated cell processes and increased numbers of pinocytic vesicles are seen.

TABLE II

Amino Acid Composition of MSP.

| Amino Acid | Residues/mole[1] | | |
|---|---|---|---|
|  | Native MSP | α Chain | β Chain |
| D | 45 | 35 | 12 |
| E | 65 | 39 | 24 |
| S | 33 | 21 | 16 |
| G | 117 | 78 | 54 |
| H | 17 | 12 | 4 |
| R | 33 | 26 | 9 |
| T | 41 | 26 | 10 |
| A | 59 | 40 | 17 |
| P | 64 | 40 | 14 |
| Y | 11 | 11 | 4 |
| V | 52 | 25 | 16 |
| M | 8 | 4 | 3 |
| I | 13 | 7 | 6 |
| L | 47 | 26 | 15 |
| F | 18 | 14 | 5 |
| K | 22 | 16 | 7 |
| Total | 645 | 420 | 216 |

[1]Based on estimated molecular masses from SDS PAGE of 70, 48 and 22 kDa for native MSP, α chain and β chain.

Statement of Deposit

A hybridoma producing mouse monoclonal IgG anti-MSP antibody was deposited on Aug. 6, 1990 at the American Type Culture Collection 12301 Parklawn Drive, Rockville, Md. 20852. The hybridoma has been assigned the ATCC accession number HB 10522. The immunoaffinity column for the purification of MSP can be made with the antibody produced by this hybridoma.

All publications mentioned hereinabove are hereby incorporated by reference.

While the foregoing invention has been described in some detail for purposes of clarity and understanding, it will be appreciated by one skilled in the art from a reading of this disclosure that various changes in form and detail can be made without departing from the true scope of the invention.

What is claimed is:

1. A purified antibody which binds Macrophage Stimulating Protein wherein said macrophage stimulating protein is characterized as having a molecular weight of 70 kilodaltons as determined by non-reducing sodium dodecyl sulfate polyacrylamide gel electrophoresis, and the subunits have molecular weights of 47 kD and 22 kD as determined by reducing sodium dodecyl sulphate polyacrylamide gel electrophoresis, and a specific activity of at least $2 \times 10^5$ units macrophage stimulating protein/mg protein.

2. An antibody according to claim 1 which is monoclonal.

3. An antibody according to claim 1 which is polyclonal.

4. A complex comprising said antibody according to claim 1 bound to a solid support.

5. A method of purifying macrophage stimulating protein comprising treating partially purified macrophage stimulating protein having a specific activity of at least 6 units macrophage stimulating protein/mg protein by anti-macrophage stimulating protein immunoaffinity column purification followed by high performance liquid chromatography and eluting therefrom macrophage stimulating protein which is characterized by a specific activity of at least $2\times10^5$ units macrophage stimulating protein/mg protein.

6. A monoclonal antibody according to claim 2 wherein the antibody binds purified macrophage stimulating protein on sodium dodecyl sulphate polyacrylamide gel electrophoresis under non-reducing conditions.

7. The monoclonal antibody produced by the hybridoma ATCC HB10522.

8. A bioassay for the detection of antibodies for macrophage stimulating protein comprising the steps of:

(a) coating a surface with purified macrophage stimulating protein wherein said macrophage stimulating protein is characterized as having a molecular weight of 70 kilodaltons as determined by non-reducing sodium dodecyl sulfate polyacrylamide gel electrophoresis, and the subunits have molecular weights of 47 kilodaltons and 22 kilodaltons as determined by reducing sodium dodecyl sulphate polyacrylamide gel, and a specific activity of at least $2\times10^5$ units macrophage stimulating protein/mg protein;

(b) contacting said coated surface with an antibody containing sample; and (c) detecting a complex formed between said protein and antibodies in said sample.

\* \* \* \* \*